United States Patent
Vaysse-Ludot et al.

(10) Patent No.: US 7,105,683 B2
(45) Date of Patent: Sep. 12, 2006

(54) PROCESS FOR THE INDUSTRIAL SYNTHESIS OF THE METHYL DIESTER OF 5-AMINO-3-CARBOXYMETHYL-4-CYANO-2-THIOPHENECARBOXYLIC ACID, AND APPLICATION TO THE SYNTHESIS OF BIVALENT SALTS OF RANELIC ACID AND THEIR HYDRATES

(75) Inventors: Lucile Vaysse-Ludot, Saint-Wandrille-Rancon (FR); Jean-Pierre Lecouve, Le Havre (FR); Pascal Langlois, Saint Jean de la Neuville (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 385 days.

(21) Appl. No.: 10/669,738

(22) Filed: Sep. 24, 2003

(65) Prior Publication Data
US 2004/0059135 A1    Mar. 25, 2004

(30) Foreign Application Priority Data
Sep. 24, 2002  (FR) .................................. 02 11764

(51) Int. Cl.
*C07D 333/02*   (2006.01)
*C07D 265/30*   (2006.01)

(52) U.S. Cl. ........................... 549/61; 544/106; 549/29

(58) Field of Classification Search .................. 549/29, 549/61; 544/106
See application file for complete search history.

(56) References Cited

FOREIGN PATENT DOCUMENTS

EP          0 415850 A1 *   3/1991
FR          EP 0415850      3/1991

OTHER PUBLICATIONS

*French Search Report for French Application No. 02.11764*, Apr. 1, 2003.
*International Preliminary Examination Report for International No. PCT/FR2003/002776*, Dec. 3, 2004.
Wierzbicki, et al., *Bull. Chim. Soc. Fr.*, 1975, 7-8, 1786-1792.

* cited by examiner

*Primary Examiner*—Golam M. M. Shameem
(74) *Attorney, Agent, or Firm*—Hueschen and Sage

(57) ABSTRACT

The process for the industrial the synthesis of the compound of formula (I):

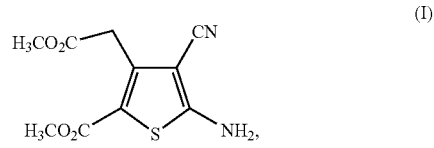

Application to the the synthesis of bivalent salts of ranelic acid and more especially strontium ranelate and its hydrates.

4 Claims, No Drawings

PROCESS FOR THE INDUSTRIAL SYNTHESIS OF THE METHYL DIESTER OF 5-AMINO-3-CARBOXYMETHYL-4-CYANO-2-THIOPHENECARBOXYLIC ACID, AND APPLICATION TO THE SYNTHESIS OF BIVALENT SALTS OF RANELIC ACID AND THEIR HYDRATES

The present invention relates to a process for the industrial synthesis of the methyl diester of 5-amino-3-carboxymethyl-4-cyano-2-thiophenecarboxylic acid and to the application thereof in the industrial production of bivalent salts of ranelic acid and their hydrates.

More specifically, the present invention relates to a new process for the industrial synthesis of the compound of formula (I):

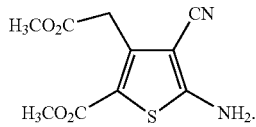

(I)

The compound of formula (I) obtained according to the process of the invention is useful in the synthesis of ranelic acid, its strontium, calcium or magnesium salts of formula (II):

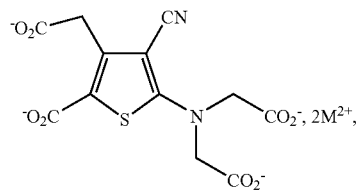

(II)

wherein M represents strontium, calcium or magnesium, and hydrates of the said salts.

BACKGROUND OF THE INVENTION

The bivalent salts of ranelic acid have very valuable pharmacological and therapeutic properties, especially pronounced anti-osteoporotic properties, making these compounds useful in the treatment of bone diseases.

DESCRIPTION OF THE PRIOR ART

The bivalent salts of ranelic acid, and more especially strontium ranelate, the preparation thereof and the therapeutic use thereof have been described in the European Patent Specification EP 0 415 850.

That Patent Specification describes the synthesis of strontium ranelate starting from the ethyl tetraester of formula (III):

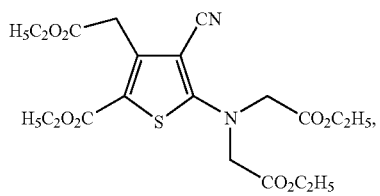

(III)

which is itself obtainable starting from the ethyl diester of formula (IV):

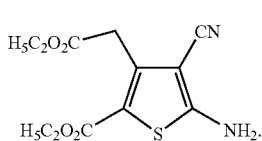

(IV)

Synthesis of the intermediate of formula (IV) has been described in the publication Bull. Soc. Chim. France 1975, pp. 1786–1792 and in the publication J. Chem. Tech. Biotechnol. 1990, 47, pp. 39–46, by reaction between diethyl 3-oxoglutarate, malononitrile and sulphur in ethanol, in the presence of morpholine or diethylamine.

That process has the advantage of using readily accessible starting materials and of being simple to put into practice; however, when transferred to the scale of several hundred kilograms, it does not allow the compound of formula (IV) to be obtained in a yield greater than 70%.

In view of the pharmaceutical interest of strontium ranelate and the tonnages produced, it has been important to be able to synthesise a diester of 5-amino-3-carboxymethyl-4-cyano-2-thiophenecarboxylic acid of excellent purity, in a yield of at least 77%, which is reproducible on an industrial scale.

DETAILED DESCRIPTION OF THE INVENTION

The Applicant has now developed an effective industrial synthesis process allowing the methyl diester of formula (I) to be obtained in a yield of at least 77% and with a purity greater than 97%.

The compound of formula (I) thereby obtained is especially useful in the synthesis of ranelic acid, its strontium, calcium or magnesium salts and hydrates of the said salts, more especially strontium ranelate and its hydrates, wherein it is reacted with an ester of bromoacetic acid to yield the corresponding tetraester, which is then converted into ranelic acid or into a strontium, calcium or magnesium salt thereof.

More specifically, the present invention relates to a process for the industrial synthesis of the compound of formula (I), which process is characterised in that dimethyl 3-oxoglutarate of formula (V):

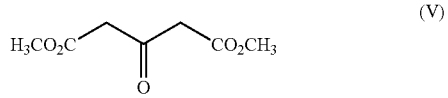

is reacted with malonitrile of formula (VI):

in methanol, in the presence of morpholine in an amount greater than 0.95 mol per mol of compound of formula (V), to yield the compound of formula (VII):

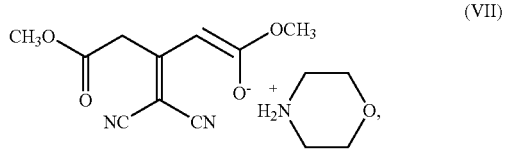

which is then reacted with sulphur in an amount greater than 0.95 mol per mol of compound of formula (V);

the reaction mixture is then heated at reflux;

and the compound of formula (I) thereby obtained is isolated by precipitation in the presence of water, followed by filtration.

The process, accordingly improved by the use of these very specific conditions, and especially by the intermediate formation of the compound of formula (VII), which can, if desired, be isolated, allows the compound of formula (I) to be obtained with excellent purity and in a yield of at least 77% which is reproducible on the scale of several hundred kilograms, which represents a major gain in yield in view of the large tonnages of strontium ranelate produced.

The amount of methanol is preferably from 1 to 3 ml per gram of compound of formula (V).

The temperature of reaction between the compounds of formulae (V) and (VI) is preferably less than 50° C.

The reaction time at reflux after addition of the sulphur is preferably from 1 hour 30 minutes to 3 hours.

Methyl 5-amino-4-cyano-3-(2-methoxy-2-oxoethyl)-2-thiophenecarboxylate of formula (I) and the intermediate of formula (VII) are new compounds which are useful as synthesis intermediates in the chemical or pharmaceutical industry, especially in the synthesis of strontium ranelate, and accordingly form an integral part of the present invention.

The Examples hereinbelow illustrate the invention but do not limit it in any way.

EXAMPLE 1

Methyl 5-amino-4-cyano-3-(2-methoxy-2-oxoethyl)-2-thiophene-carboxylate

Introduce into a reactor 400 kg of dimethyl 3-oxoglutarate, 158 kg of malononitrile and 560 litres of methanol and then, whilst maintaining the temperature of the reaction mixture below 40° C., 199.6 kg of morpholine.

Then introduce 73.6 kg of sulphur and subsequently bring the mixture to reflux.

After reacting for 2 hours, stop refluxing and add water until precipitation occurs. Filter off the precipitate obtained, wash it and dry it.

Methyl 5-amino-4-cyano-3-(2-methoxy-2-oxoethyl)-2-thiophenecarboxylate is thereby obtained in a yield of 77% and with a chemical purity of 98%.

EXAMPLE 2

Methyl 5-amino-4-cyano-3-(2-methoxy-2-oxoethyl)-2-thiophene-carboxylate

Introduce into a reactor 400 kg of dimethyl 3-oxoglutarate, 158 kg of malononitrile and 560 liters of methanol and then, whilst maintaining the temperature of the reaction mixture below 40° C., 199.6 kg of morpholine.

The compound of formula (VII) thereby obtained, or the addition salt of methyl 3-(dicyanomethylene)-5-hydroxy-5-methoxy-4-pentenoate with morpholine, is isolated by filtration after cooling of the mixture and is then reacted with 73.6 kg of sulphur in methanol.

The mixture is then brought to reflux.

After reacting for 2 hours, stop refluxing and add water until precipitation occurs. Filter off the precipitate obtained, wash it and dry it.

What is claimed is:

1. A process for the industrial synthesis of the compound of formula (I):

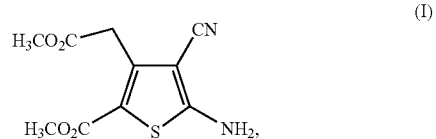

wherein dimethyl 3-oxoglutarate of formula (V):

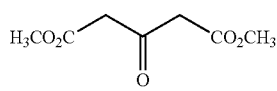

is reacted with malononitrile of formula (VI):

in methanol, in the presence of morpholine in an amount greater than 0.95 mol per mol of compound of formula (V), to yield the compound of formula (VII):

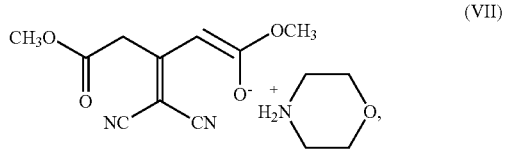

which is then reacted with sulphur in an amount greater than 0.95 mol per mol of compound of formula (V);

the reaction mixture is then heated at reflux;

and the compound of formula (I) thereby obtained is isolated by precipitation in the presence of water, followed by filtration.

2. The synthesis process of claim 1, wherein the amount of methanol is from 1 to 3 ml per gram of compound of formula (V).

3. The synthesis process of claim 1, wherein the temperature of reaction between the compounds of formulae (V) and (VI) is less than 500° C.

4. The synthesis process of claim 1, wherein the reaction time at reflux after addition of the sulphur is from 1 hour 30 minutes to 3 hours.

* * * * *

UNITED STATES PATENT AND TRADEMARK OFFICE
CERTIFICATE OF CORRECTION

PATENT NO.       : 7,105,683 B2                                              Page 1 of 1
APPLICATION NO.  : 10/669738
DATED            : September 12, 2006
INVENTOR(S)      : Lucile Vaysse-Ludot et al.

It is certified that error appears in the above-identified patent and that said Letters Patent is hereby corrected as shown below:

Column 6, Line 10:    "500°" should be -- 50° --.

Signed and Sealed this

Seventh Day of November, 2006

JON W. DUDAS
*Director of the United States Patent and Trademark Office*